US00PP20263P2

(12) United States Plant Patent
Stever

(10) Patent No.: US PP20,263 P2
(45) Date of Patent: Sep. 1, 2009

(54) ***ALTERNANTHERA* PLANT NAMED 'MAI TAI'**

(50) Latin Name: *Alternanthera ficoidea*
Varietal Denomination: Mai Tai

(75) Inventor: Karen Stever, Gainesville, GA (US)

(73) Assignee: ItSaul Plants LLC, Alpharetta, GA (US)

( * ) Notice: Subject to any disclaimer, the term of this patent is extended or adjusted under 35 U.S.C. 154(b) by 0 days.

(21) Appl. No.: 12/215,881

(22) Filed: Jun. 30, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Alternanthera* plant named 'Mai Tai', characterized by its upright to outwardly spreading plant habit; freely branching habit; dense and bushy growth habit; strong and healthy leaves; variegated leaves that are dark burgundy/brown, red purple, green and creamy white in color; and good garden performance.

1 Drawing Sheet

Botanical designation: *Alternanthera ficoidea.*
Cultivar denomination: 'Mai Tai'.

BACKGROUND OF THE INVENTION

The present invention relates to a new and distinct cultivar of *Alternanthera,* botanically known as *Alternanthera ficoidea* and hereinafter referred to by the name 'Mai Tai'.

The new *Alternanthera* is a naturally-occurring branch mutation of *Alternanthera ficoidea* 'Partytime', disclosed in U.S. Plant Pat. No. 14,789. The new *Alternanthera* was discovered and selected by the Inventor from within a population of plants of the parent selection in a controlled greenhouse environment in Alpharetta, Ga. in June, 2006.

Asexual reproduction of the new *Alternanthera* by vegetative cuttings in a controlled greenhouse environment in Alpharetta, Ga. since June, 2006, has shown that the unique features of this new *Alternanthera* are stable and reproduced true to type in successive generations.

SUMMARY OF THE INVENTION

Plants of the new *Alternanthera* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Mai Tai'. These characteristics in combination distinguish 'Mai Tai' as a new and distinct cultivar of *Alternanthera:*

1. Upright to outwardly spreading plant habit.
2. Freely branching habit; dense and bushy growth habit.
3. Strong and healthy leaves.
4. Variegated leaves that are dark burgundy/brown, red purple, green and creamy white in color.
5. Good garden performance.

Plants of the new *Alternanthera* differ primarily from plants of the parent, 'Partytime', in the following characteristics:

1. Plants of the new *Alternanthera* have slightly larger leaves than plants of 'Partytime'.
2. Plants of the new *Alternanthera* and 'Partytime' differ in leaf color as plants of 'Partytime' had green, creamy white and red purple-colored leaves.

Plants of the new *Alternanthera* can be compared to plants of *Alternanthera ficoidea* 'Grenadine', disclosed in U.S. Plant Pat. No. 16,442. In side-by-side comparisons conducted in Alpharetta, Ga., plants of the new *Alternanthera* differed from plants of 'Grenadine' in the following characteristics:

1. Plants of the new *Alternanthera* were more vigorous and taller than plants of 'Grenadine'.
2. Plants of the new *Alternanthera* had thicker stems than plants of 'Grenadine'.
3. Plants of the new *Alternanthera* had larger leaves than plants of 'Grenadine'.
4. Plants of the new *Alternanthera* and 'Grenadine' differed in leaf color as plants of 'Grenadine' had brown and red purple bi-colored leaves.

BRIEF DESCRIPTION OF THE PHOTOGRAPH

The accompanying colored photograph illustrates the overall appearance of the new *Alternanthera,* showing the colors as true as it is reasonably possible to obtain in colored reproductions of this type. Colors in the photograph may differ slightly from the color values cited in the detailed botanical description which accurately describe the colors of the new *Alternanthera.* The photograph comprises a top perspective view of a typical plant of 'Mai Tai' grown in an outdoor nursery.

DETAILED BOTANICAL DESCRIPTION

The aforementioned photograph and following observations, measurements and values describe plants grown during the spring and summer in an outdoor nursery in north central Texas. Plants had been growing for a year in the outdoor nursery when the photograph and description were taken. In the following description, color references are made to The Royal Horticultural Society Colour Chart, 1995 Edition, except where general terms of ordinary dictionary significance are used.

Botanical classification: *Alternanthera ficoidea* 'Mai Tai'.

Parentage: Naturally-occurring branch mutation of *Alternanthera ficoidea* 'Partytime', disclosed in U.S. Plant Pat. No. 14,789.

Propagation:

*Type.*—By vegetative cuttings.

*Time to initiate roots, summer.*—About one week at 24° C.

*Time to initiate roots, winter.*—About two weeks at 18° C.

*Time to produce a rooted young plant, summer.*—About four weeks at 24° C.

*Time to produce a rooted young plant, winter.*—About five weeks at 18° C.

*Root description.*—Thin, fibrous; white in color.

*Rooting habit.*—Freely branching; dense.

Plant description:

*Plant form and growth habit.*—Upright to outwardly spreading plant habit; herbaceous subshrub. Short internodes; densely foliated. Moderately vigorous growth rate.

*Branching habit.*—Freely basal branching habit with lateral branches potentially forming at every internode.

*Plant height.*—About 26 cm.

*Plant diameter.*—About 45 cm.

*Lateral branch description.*—Length: About 42 cm. Diameter: About 5 mm. Internode length: About 3.2 cm. Strength: Strong; flexible. Texture, younger stems: Smooth, glabrous. Texture, mature stems: Pubescent. Color, developing stems: Close to 146A flushed with close to 59A. Color, older stems: Close to 58A.

*Leaf description.*—Arrangement: Opposite; simple; strong and healthy leaves. Length: About 4.5 cm. Width: About 3.3 cm. Shape: Ovate. Apex: Acuminate. Base: Cordate with truncate tendencies. Margin: Entire; undulate. Texture, upper surface: Smooth, glabrous; rugose. Texture, lower surface: Pubescent; rugose. Venation: Pinnate. Color: Developing and fully expanded leaves, upper surface: Random sectors of close to 8D, close to 144A, between 58A and 61A or close to 200A to 200B; midvein, close to 59A; lateral venation, similar to lamina. Developing and fully expanded leaves, lower surface: Random sectors of close to 8D, close to 144A, between 58A and 61A (dulled) and close to 200B flushed with close to 59A; midvein, close to 58A; lateral venation, similar to lamina. Petiole: Length: About 1.4 cm. Diameter: About 1.5 mm. Texture, upper surface: Smooth, glabrous. Texture, lower surface: Pubescent. Color, upper surface: Close to 59A. Color, lower surface: Close to 58A.

Flower description: Flower development as not been observed on plants of the new *Alternanthera.*

Disease/pest resistance: Plants of the new *Alternanthera* have not been observed to be resistant to pathogens and pests common to *Alternanthera.*

Garden performance: Plants of the new *Alternanthera* have been observed to have good garden performance and tolerate rain, wind and temperatures ranging from about 4° C. to about 40° C.

It is claimed:

1. A new and distinct *Alternanthera* plant named 'Mai Tai' as illustrated and described.

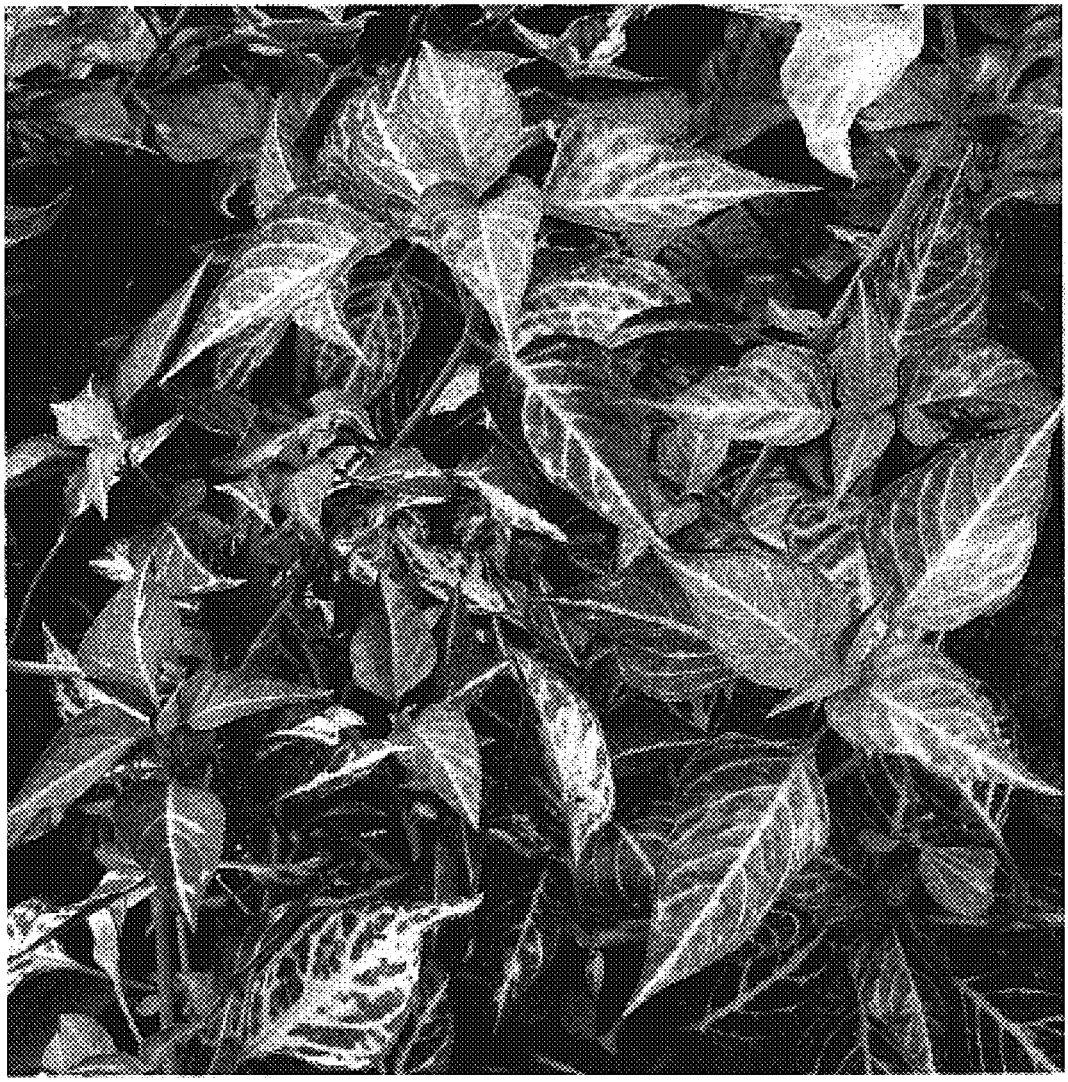

* * * * *